(12) United States Patent
Kimura et al.

(10) Patent No.: US 7,977,418 B2
(45) Date of Patent: Jul. 12, 2011

(54) BISPHENOL MONOESTER-BASED STABILIZER COMPOSITION, THERMOPLASTIC POLYMER COMPOSITION AND METHOD OF MANUFACTURING THE SAME, THERMOPLASTIC POLYMER MOLDED PRODUCT, AND METHOD OF STABILIZING THERMOPLASTIC POLYMER

(75) Inventors: Kenji Kimura, Toyonaka (JP); Ryoji Soma, Nara (JP); Masatsugu Akiba, Toyonaka (JP); Toyomochi Tamato, Nishinomiya (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 301 days.

(21) Appl. No.: 12/219,384

(22) Filed: Jul. 21, 2008

(65) Prior Publication Data
US 2009/0043027 A1    Feb. 12, 2009

(30) Foreign Application Priority Data

Jul. 25, 2007    (JP) .................................. 2007-193691

(51) Int. Cl.
C08K 5/00    (2006.01)
C07C 69/00    (2006.01)
C09K 15/00    (2006.01)

(52) U.S. Cl. .......... 524/291; 560/138; 560/140; 252/404

(58) Field of Classification Search .................. 524/293, 524/291, 302, 289; 528/193, 206; 252/404, 252/181.12, 182.29; 560/138, 140, 101; 525/50

See application file for complete search history.

(56) References Cited

U.S. PATENT DOCUMENTS

| 3,984,372 A | 10/1976 | Cottman |
| 4,365,032 A | 12/1982 | Yosizato et al. |
| 4,774,274 A * | 9/1988 | Takata et al. .................. 524/291 |
| 5,128,398 A * | 7/1992 | Sasaki et al. .................. 524/291 |
| 5,214,193 A * | 5/1993 | Inoue et al. .................... 560/140 |
| 6,861,552 B2 | 3/2005 | Yamamoto et al. |

FOREIGN PATENT DOCUMENTS

| EP | 0 144 477 A1 | 6/1985 |
| EP | 0 322 166 A1 | 6/1989 |
| EP | 1306363 A1 | 5/2003 |
| GB | 2 042 512 A | 9/1980 |
| JP | 1-168643 | 7/1989 |
| JP | 03-088841 | 4/1991 |
| JP | 04-327558 | 11/1992 |
| JP | 2006-176419 | 7/2006 |

OTHER PUBLICATIONS

Office Action in U.S. Appl. No. 12/219,145 dated Dec. 11, 2008.
Office Action in U.S. Appl. No. 12/219,145 dated Aug. 21, 2009.

* cited by examiner

Primary Examiner — Vasu Jagannathan
Assistant Examiner — Hannah Pak
(74) Attorney, Agent, or Firm — Foley & Lardner LLP

(57) ABSTRACT

The present invention provides a bisphenol monoester-based stabilizer composition that can improve resistance to discoloration at high temperature of a thermoplastic polymer compared with a conventional one using a bisphenol monoester-based stabilizer composition including a bisphenol monoester-based compound mainly, wherein a compound represented by the following formula:

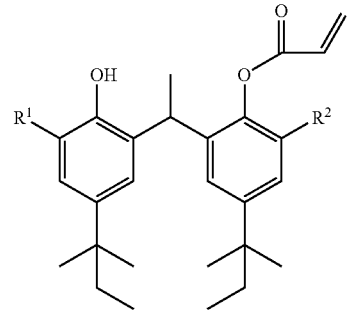

is contained in an area percentage by liquid chromatography analysis of 0.1 to 3%, a thermoplastic polymer composition and a method of manufacturing the thermoplastic polymer composition, a thermoplastic polymer molded product, and a method of stabilizing a thermoplastic polymer, as well as a thermoplastic polymer composition in which resistance to discoloration at high temperature is improved by using the stabilizer composition and a method of manufacturing the thermoplastic polymer composition, a thermoplastic polymer molded product, and a method of stabilizing a thermoplastic polymer.

6 Claims, 2 Drawing Sheets

BISPHENOL MONOESTER-BASED STABILIZER COMPOSITION, THERMOPLASTIC POLYMER COMPOSITION AND METHOD OF MANUFACTURING THE SAME, THERMOPLASTIC POLYMER MOLDED PRODUCT, AND METHOD OF STABILIZING THERMOPLASTIC POLYMER

BACKGROUND OF THE INVENTION

1. Field of the Invention

The present invention relates to a bisphenol monoester-based stabilizer composition, a thermoplastic polymer composition and a method of manufacturing the same, a thermoplastic polymer molded product, and a method of stabilizing a thermoplastic polymer.

2. Description of the Background Art

In order to improve physical properties of a thermoplastic polymer such as process stability and resistance to discoloration at high temperature, a method of adding a bisphenol monoester-based compound represented by the following formula:

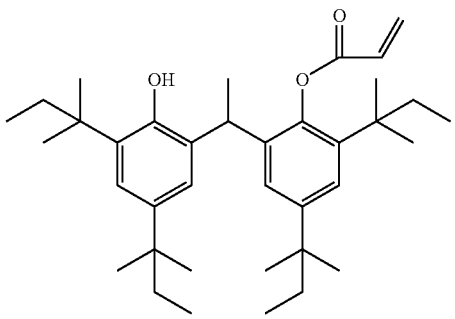

to a thermoplastic polymer is known (for example, see Japanese Patent Laying-Open No. 01-168643 (Patent Document 1)). This bisphenol monoester-based compound is normally manufactured by condensing 2 mol of 2,4-di-tert-pentylphenol with 1 mol of acetaldehyde and then reacting the condensate with an acrylic acid-based compound in a ratio of 1 mol, as shown by the following scheme:

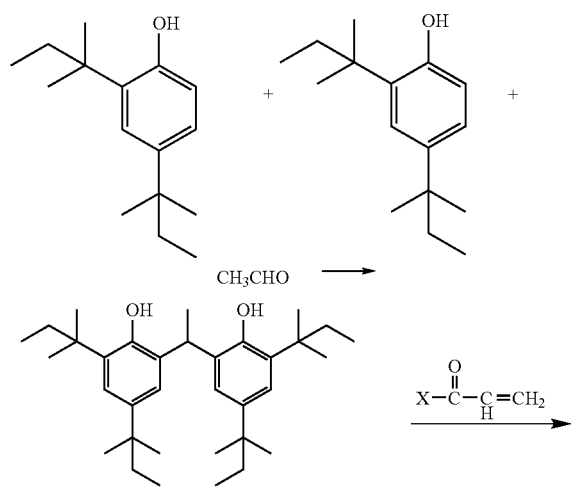

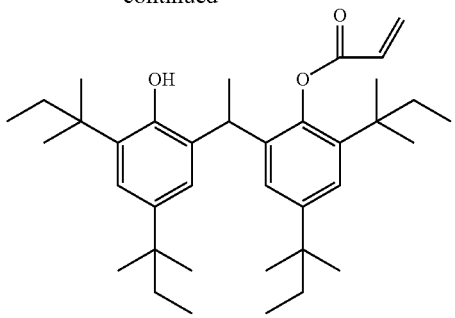

in the above-described scheme, X in the formula showing an acrylic acid-based compound represents halogen, a hydroxy group, an alkoxy group having 1 to 3 carbon atoms, or a group represented by the following formula:

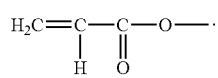

However, development of a technique that can improve the resistance to discoloration at high temperature of the thermoplastic polymer compared with the conventional method of adding such a bisphenol monoester-based compound into the thermoplastic polymer is desired.

SUMMARY OF THE INVENTION

The present invention has been made to solve the above-described problem, and an object of the present invention is to provide a bisphenol monoester-based stabilizer composition that can improve the resistance to discoloration at high temperature of a thermoplastic polymer compared with a conventional one, a thermoplastic polymer composition in which the resistance to discoloration at high temperature is improved using the stabilizer composition and a method of manufacturing the thermoplastic polymer composition, a thermoplastic polymer molded product, and a method of stabilizing a thermoplastic polymer.

The bisphenol monoester-based stabilizer composition of the present invention is characterized by a bisphenol monoester-based stabilizer composition obtained by condensing a dialkylphenol composition having 2,4-di-tert-pentylphenol as a main component and containing a compound represented by the following formula (1):

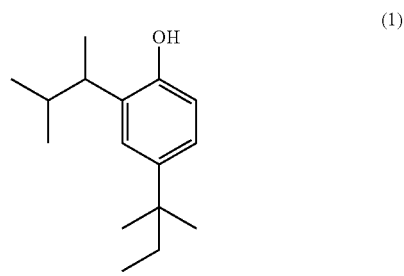

with acetaldehyde in a ratio of 1 mol with respect to 2.00 mol of a phenolic hydroxy group in the dialkylphenol composition, and then reacting the condensate with an acrylic acid-based compound, in a ratio of 1 mol, represented by the following formula (2):

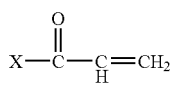

(2)

wherein x represents halogen, a hydroxy group, an alkoxy group having 1 to 3 carbon atoms, or a group represented by the following formula:

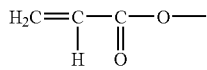

(below, the bisphenol monoester-based stabilizer composition is referred to as a "stabilizer composition according to a first aspect of the present invention").

2,4-di-tert-pentylphenol as a main component means that the content of 2,4-di-tert-pentylphenol in a dialkylphenol composition is 50% by weight or more.

The stabilizer composition according to the first aspect of the present invention is preferably a composition in which the above-described dialkylphenol composition contains the compound represented by the formula (1) in an area percentage by liquid chromatography analysis of 0.5 to 20%.

The present invention also provides a thermoplastic polymer composition containing a thermoplastic polymer and 0.005 to 5 parts by weight of the stabilizer composition according to the first aspect of the present invention described above with respect to 100 parts by weight of the thermoplastic polymer.

The present invention also provides a thermoplastic polymer molded product containing a thermoplastic polymer and 0.005 to 5 parts by weight of the stabilizer composition according to the first aspect of the present invention described above with respect to 100 parts by weight of the thermoplastic polymer.

The present invention also provides a method of stabilizing a thermoplastic polymer characterized by compounding the stabilizer composition according to the first aspect of the present invention described above into the thermoplastic polymer.

The present invention also provides a method of manufacturing the thermoplastic polymer composition characterized by compounding 0.005 to 5 parts by weight of the stabilizer composition according to the first aspect of the present invention described above into 100 parts by weight of the thermoplastic polymer.

The present invention also provides a bisphenol monoester-based stabilizer composition mainly including a bisphenol monoester-based compound represented by the following formula (3):

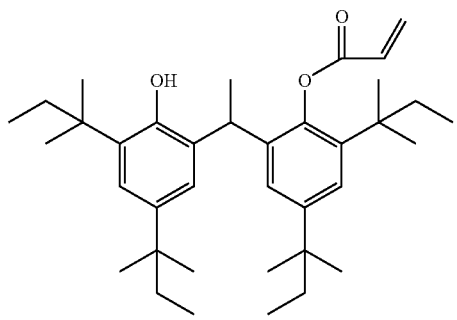

(3)

wherein a compound represented by the following formula (4):

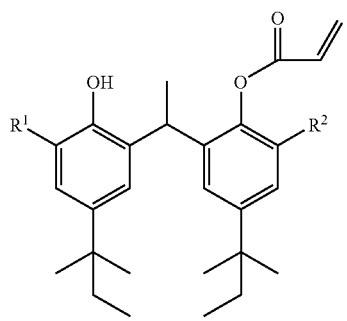

(4)

wherein any one of $R^1$ and $R^2$ represents a tert-pentyl group and the other represents a 1,2-dimethylpropyl group, is contained in an area percentage by liquid chromatography analysis of 0.1 to 3% (below, the bisphenol monoester-based stabilizer composition is referred to as a "stabilizer composition according to a second aspect of the present invention").

In the stabilizer composition according to the second aspect of the present invention, the content of the composition represented by the formula (4) is preferably 0.1 to 1.5% in area percentage by liquid chromatography analysis.

Further, the present invention also provides a thermoplastic polymer composition containing a thermoplastic polymer and the stabilizer composition according to the second aspect of the present invention described above. This thermoplastic polymer composition preferably contains 0.005 to 5 parts by weight of the stabilizer composition according to the second aspect of the present invention described above with respect to 100 parts by weight of the thermoplastic polymer.

The present invention also provides a thermoplastic polymer molded product containing the thermoplastic polymer and the stabilizer composition according to the second aspect of the present invention described above.

The present invention also provides a method of stabilizing a thermoplastic polymer characterized by compounding the stabilizer composition according to the second aspect of the present invention described above into the thermoplastic polymer.

The present invention also provides a method of manufacturing the thermoplastic polymer composition characterized by compounding 0.005 to 5 parts by weight of the stabilizer composition according to the second aspect of the present invention described above is compounded into 100 parts by weight of the thermoplastic polymer.

According to the present invention, a bisphenol monoester-based stabilizer composition that can improve the resistance to discoloration at high temperature of a thermoplastic polymer compared with the conventional one, a thermoplastic polymer composition using the stabilizer composition and a method of manufacturing the thermoplastic polymer composition, a thermoplastic polymer molded product, and a method of stabilizing a thermoplastic polymer can be provided.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

<Bisphenol Monoester-Based Stabilizer Composition>

Figure 1:
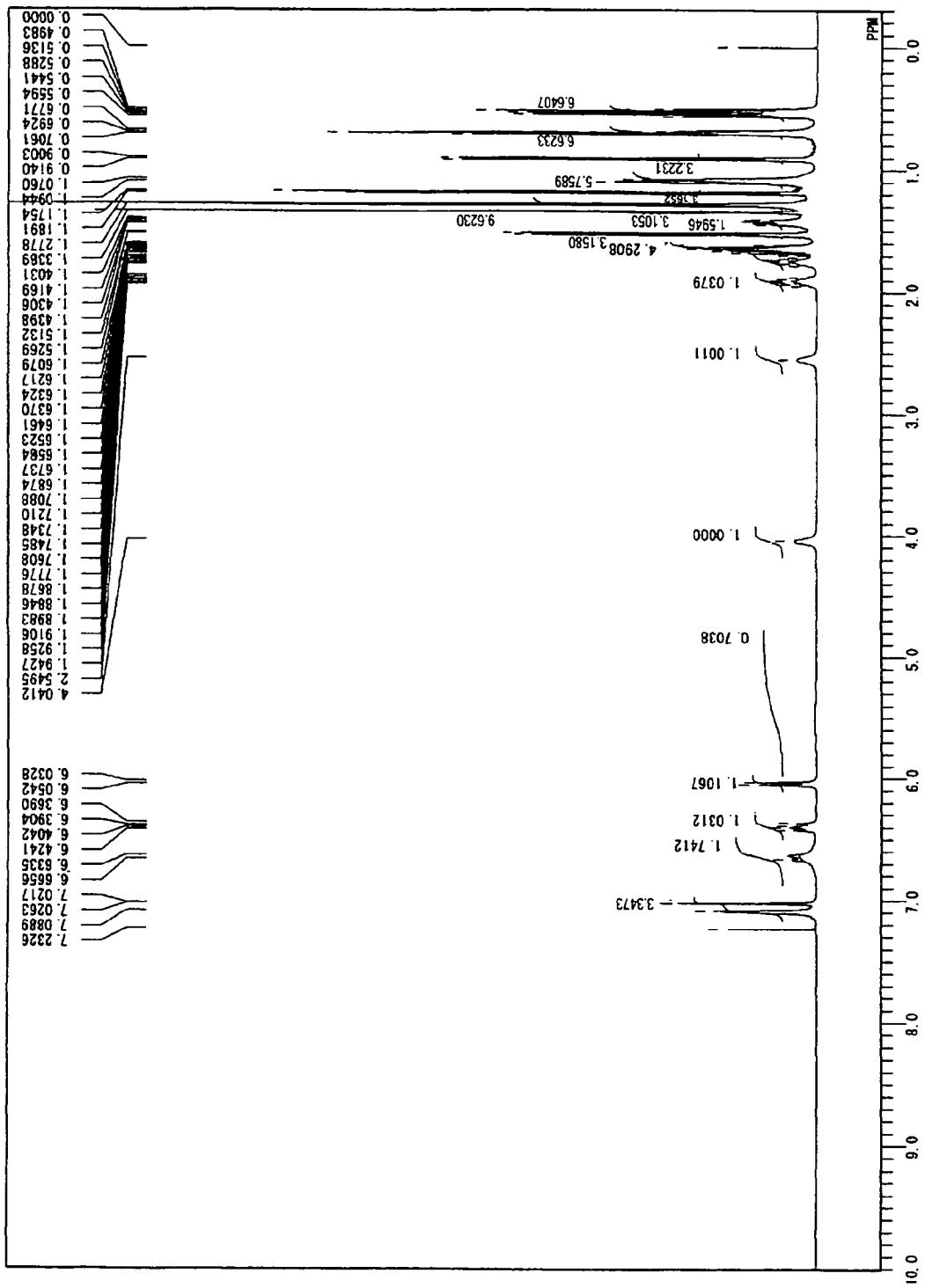
FIG. 1 is a $^1$H NMR spectrum of a bisphenol monoester-based compound represented by the formula (4) and fractionated in Example 1.

The bisphenol monoester-based stabilizer composition of the present invention (the stabilizer composition according to the first aspect of the present invention) is obtained by using a dialkylphenol composition having 2,4-di-tert-pentylphenol represented by the following formula:

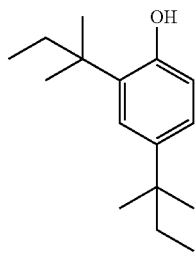

as a main component, and containing a compound represented by the following formula (1):

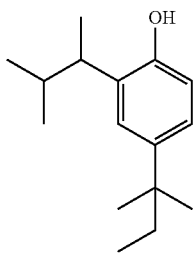
(1)

as a raw material. The dialkylphenol composition of the present invention preferably contains the compound represented by the formula (1) in an area percentage by liquid chromatography of 0.5 to 20% from the viewpoint of great improvement in resistance to discoloration at high temperature of the thermoplastic polymer containing the composition, more preferably, 0.5 to 10%.

Further, since the compound represented by the formula (1) is contained in an area percentage by liquid chromatography of 0.5 to 20% as the above-described dialkylphenol composition, a compound represented by the following formula (4):

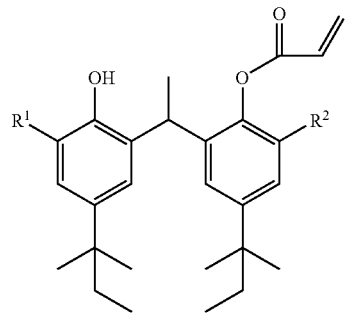
(4)

wherein any one of $R^1$ and $R^2$ represents a tert-pentyl group and the other represents a 1,2-dimethylpropyl group, can be contained in the bisphenol monoester-based stabilizer composition of the present invention in an area percentage by liquid chromatography analysis of 0.1 to 3%. As a result, the above-described resistance to discoloration at high temperature can be improved.

Here, as a method of measuring the area percentage of the compound represented by the formula (4) in the bisphenol monoester-based stabilizer composition of the present invention by liquid chromatography, using LC-10A (manufactured by Shimadzu Corporation) with Sumipax A-210EC (manufactured by Sumika Chemical Analysis Service, Ltd., 3 mm in diameter×15 cm in length, diameter of filler: 5 μm) as a column and a mixed solution of water and acetonitrile as a mobile phase, the ratio of acetonitrile in the mobile phase is increased from 75% at 0.42%/minute and the ratio is kept 100% for 20 minutes, and a value is calculated from peak area measured with an UV detector at 280 nm in the above-described condition.

Moreover, any of the liquid chromatography analysis of the present invention is performed in the same manner as the measuring method described above.

The stabilizer composition according to the first aspect of the present invention is characterized by a stabilizer composition obtained by condensing the dialkylphenol composition described above with acetaldehyde in a ratio of 1 mol, preferably 0.98 to 1.40 mol, and particularly preferably 1.00 to 1.20 mol with respect to 2.00 mol of the phenolic hydroxy group contained in the dialkylphenol composition, and then reacting the condensate with the acrylic acid-based compound represented by the following formula (2) in a ratio of 1 mol, preferably 0.98 to 1.40 mol, and particularly preferably 1.00 to 1.20 mol.

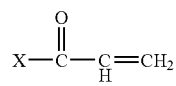
(2)

In the formula (2), X represents halogen, a hydroxy group, an alkoxy group having 1 to 3 carbon atoms, or a group represented by the following formula:

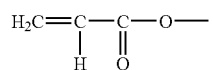

Among these, X in the formula (2) is preferably a halogen because of its high reactivity. Examples of the halogen in the acrylic acid-based compound used in the present invention include a fluorine atom, a chlorine atom, a bromine atom, an iodine atom and the like, and among these, the chlorine atom is preferable from the viewpoints of its high reactivity and ease of its handling. Further, in the case where X in the acrylic acid-based compound used in the present invention is a hydroxy group, there is an advantage that byproducts are less. Further, examples of the alkoxy group having 1 to 3 carbon atoms in the acrylic acid-based compound used in the present invention include a methoxy group, an ethoxy group, and a propoxy group, and among these, the methoxy group is preferable because removal of free alcohol is easy.

Moreover, in the stabilizer composition according to the first aspect of the present invention, conditions (solvent, temperature, time, and the like) of the condensation reaction of the above-described dialkylphenol composition and acetaldehyde, and the conditions of the reaction of the condensate obtained in the above-described condensation reaction and the above-described acrylic acid-based compound are not particularly limited, and appropriate conditions that have been widely applied conventionally when manufacturing a bisphenol monoester-based compound may be used.

Further, the present invention also provides a bisphenol monoester-based stabilizer composition (the stabilizer composition according to the second aspect) mainly including a bisphenol monoester-based compound represented by the following formula (3):

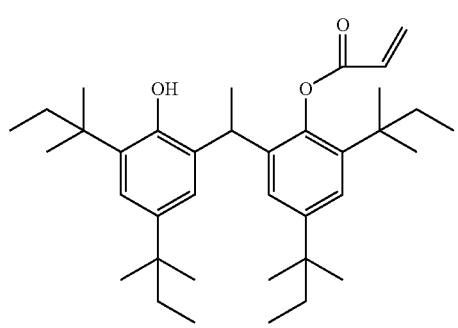

(3)

wherein a compound represented by the following formula (4):

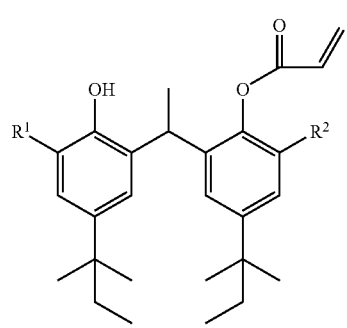

(4)

wherein any one of $R^1$ and $R^2$ represents a tert-pentyl group and the other represents an 1,2-dimethylpropyl group, is contained.

In the stabilizer composition according to the second aspect of the present invention, the compound represented by the formula (4) is contained in an area percentage by liquid chromatography analysis of 0.05 to 3%, and preferably 0.1 to 1.5%, from the viewpoint of great improvement in resistance to discoloration at high temperature of the thermoplastic polymer containing the composition.

As described above for the stabilizer composition according to the first aspect of the present invention, the stabilizer composition according to the second aspect of the present invention is preferably manufactured by condensing a dialkylphenol composition having 2,4-di-tert-pentylphenol as a main component and containing the compound represented by the formula (1) with acetaldehyde in a ratio of 1 mol, preferably 0.90 to 1.40 mol, and particularly preferably 0.95 to 1.20 mol with respect to 2.00 mol of the phenolic hydroxy group contained in the dialkylphenol composition, and then reacting the condensate with the acrylic acid-based compound represented by the formula (2) in a ratio of 1 mol, preferably 0.90 to 1.40 mol, and particularly preferably 0.95 to 1.20 mol. However, it is not limited to the compositions that are manufactured in such a way as long as it has the compositions described above.

The stabilizer composition according to the first aspect of the present invention and the stabilizer composition according to the second aspect of the present invention described above (below, these are generically referred to as a "stabilizer composition of the present invention") can improve the resistance to discoloration at high temperature of the thermoplastic polymer compared with the conventional one. Here, the improvement of the resistance to discoloration at high temperature can be evaluated by kneading a thermoplastic polymer composition obtained by compounding the stabilizer of the present invention into a thermoplastic polymer, molding the thermoplastic polymer composition into a sheet form having a thickness of 1 mm with a pressing machine, and measuring a yellowness index (YI) value using a colorimeter in accordance with JIS K7105. The smaller the measured YI value is, the higher the resistance to discoloration at high temperature is meant to be.

Conventionally known appropriate additives may be, of course, added to the stabilizer composition of the present invention in a range of which the effect of the present invention is not hindered. Examples of such additives include an ultraviolet absorber, a light stabilizer, an antioxidant, a metal inactivator, a nucleating agent, a lubricant, an antistatic agent, a fire retardant, a filler, a pigment, a plasticizer, an antiblocking agent, a surfactant, a processing aid, a foaming agent, an emulsifier, a brightener, a neutralizing agent such as calcium stearate and hydrotalcite, a binder and the like.

Examples of a compound that may be obtained as a byproduct are as follows.

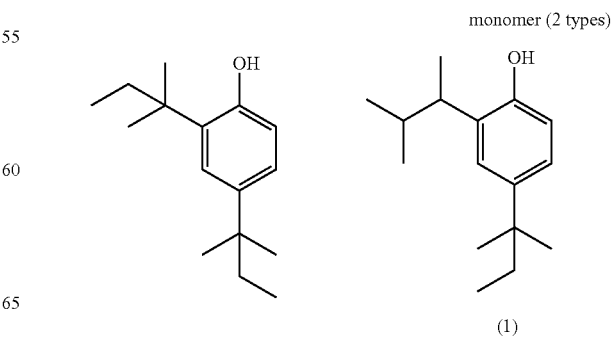

monomer (2 types)

(1)

bisphenol (3 types)

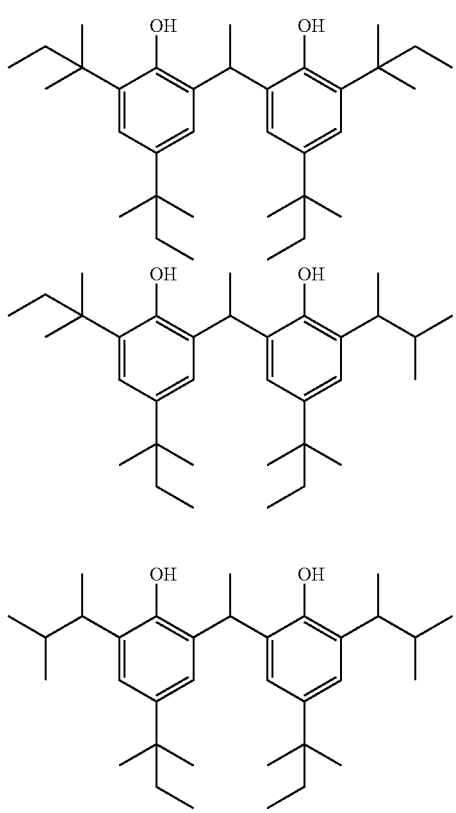

bisphenol monoester (4 types)

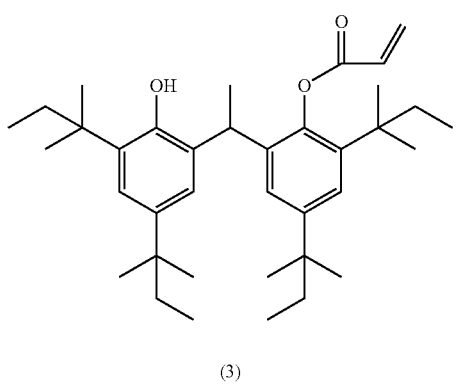

(3)

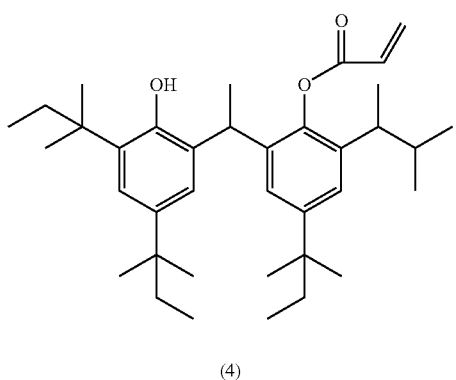

(4)

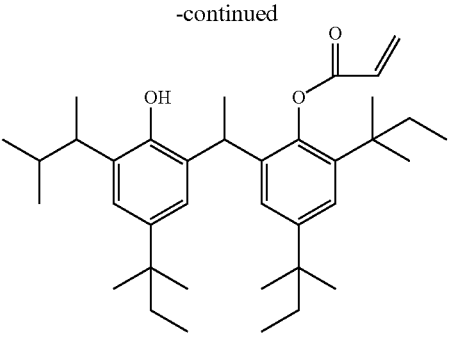

(4)

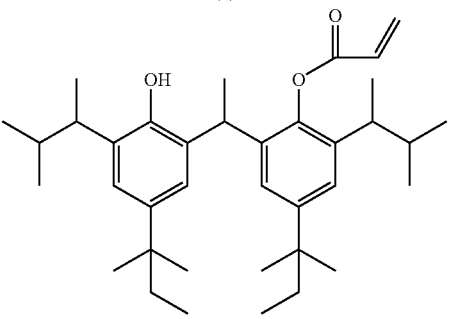

(4)

<Thermoplastic Polymer Composition>

The present invention also provides a thermoplastic polymer composition obtained by compounding 0.005 to 5 parts by weight of the stabilizer composition according to the first aspect of the present invention described above into 1 00 parts by weight of the thermoplastic polymer. The compounding amount of the stabilizer composition according to the first aspect of the present invention is preferably 0.005 part by weight or more with respect to 100 parts by weight of the thermoplastic polymer because there is a tendency of preventing the thermoplastic polymer from deteriorating during a molding process. Further, when the compounding amount of the stabilizer composition according to the first aspect of the present invention is 5 parts by weight or less with respect to 100 parts by weight of the thermoplastic polymer, there is an advantage of suppressing the appearance of a bleeding phenomenon in which the stabilizer appears on the surface of the polymer. The stabilizer composition according to the first aspect of the present invention is preferably compounded in an amount of 0.005 to 1 parts by weight with respect to 100 parts by weight of the thermoplastic polymer, and particularly preferably in an amount of 0.01 to 1 part by weight with respect to 100 parts by weight of the thermoplastic polymer.

Further, the present invention also provides a thermoplastic polymer composition obtained by compounding the stabilizer composition according to the second aspect of the present invention described above into the thermoplastic polymer. Also in such a thermoplastic polymer compositions, for the same reasons described for the thermoplastic polymer composition in which the stabilizer composition according to the first aspect of the present invention described above is compounded, the stabilizer composition according to the second aspect of the present invention is preferably compounded in an amount of 0.005 to 5 parts by weight with respect to 100 parts by weight of the thermoplastic polymer, more preferably 0.005 to 1 parts by weight, and particularly preferably 0.01 to 1 part by weight.

In the thermoplastic polymer of the present invention, resistance to discoloration at high temperature of the thermoplastic polymer is improved compared with the conventional one by compounding the stabilizer composition of the present invention as described above. The thermoplastic polymer in the thermoplastic polymer composition of the present invention normally includes a polypropylene-based resin such as an ethylene-propylene copolymer, a polyethylene-based resin (such as high-density polyethylene (HD-PE), low-density polyethylene (LD-PE), and linear low-density polyethylene (LLDPE)), a methylpentene polymer, an ethylene-ethyl acrylate copolymer, an ethylene-vinyl acetate copolymer, polystyrenes (polystyrene such as poly(p-methylstyrene) and poly(α-methylstyrene), an acrylonitrile-styrene copolymer, an acrylonitrile-butadiene-styrene copolymer, a special acrylic rubber-acrylonitrile-styrene copolymer, an acrylonitrile-chlorinated polyethylene-styrene copolymer, a styrene-butadiene copolymer, and the like), chlorinated polyethylene, polychloropyrene, a chlorinated rubber, polyvinyl chloride, polyvinylidene chloride, a methacrylic resin, an ethylene-vinylalcohol copolymer, a fluorine resin, polyacetal, a grafted polyphenylene ether resin, a polypehnylene sulfide resin, polyurethane, polyamide, a polyester resin (such as polyethylene terephthalate and polybutylene terephthalate), polycarbonate, polyacrylate, polysulfone, polyetheretherketone, polyethersulfone, an aromatic polyester resin, a diallylphthalate prepolymer, a silicone resin, 1,2-polybutadiene, polyisoprene, a butadiene-acrylonitrile copolymer, an ethylene-methylmethacrylate copolymer and the like. Among these, the polyethylene-based resin, the polypropylene-based resin, and the polystyrenes are preferable due to good molding processability, and particularly the polypropylene-based resin, the acrylonitrile-butadiene-styrene copolymer, and the styrene-butadiene copolymer are preferable.

Here, the polypropylene-based resin means polyolefin containing a structural unit originated from propylene, and specific examples include a crystalline propylene homopolymer, a propylene-ethylene random copolymer, a propylene-α-olefin random copolymer, a propylene-ethylene-α-olefin copolymer, a polypropylene-based block copolymer including a polypropylene homopolymer component or a copolymer component mainly including propylene, and a copolymer component of propylene and ethylene and/or α-olefin, and the like.

In the case of using the polypropylene-based resin as the thermoplastic polymer in the present invention, one type of the polypropylene-based resin may be used, or two or more types may be blended and used.

The α-olefin is normally α-olefin having 4 to 12 carbon atoms, and examples thereof include 1-butene, 1-pentene, 1-hexene, 4-methyl-1-pentene, 1-octene, 1-decene and the like. 1-butene, 1-hexane, and 1-octene are more preferable.

Examples of the propylene-α-olefin random copolymer include a propylene-1-butene random copolymer, a propylene-1-hexene random copolymer, a propylene-1-octene random copolymer and the like.

Examples of the propylene-ethylene-α-olefin copolymer include a propylene-ethylene-1-butene copolymer, a propylene-ethylene-1-hexene copolymer, a propylene-ethylene-1-octene copolymer and the like.

Examples of the copolymer component mainly including propylene in the polypropylene-based block copolymer including the polypropylene homopolymer component or the copolymer component mainly including propylene, and the copolymer component of propylene and ethylene and/or α-olefin include a propylene-ethylene copolymer component, a propylene-1butene copolymer component, a propylene-1-hexene copolymer component and the like. Examples of the copolymer component of propylene and ethylene and/or α-olefin include a propylene-ethylene copolymer component, a propylene-ethylene-1-butene copolymer component, a propylene-ethylene-1hexene copolymer component, a propylene-ethylene-1-octene copolymer component, a propylene-1butene copolymer component, a propylene-1hexene copolymer component, a propylene-1octene copolymer component and the like. Moreover, the content of ethylene and/or α-olefin having 4 to 12 carbon atoms in the copolymer component of propylene and ethylene and/or α-olefin is normally 0.01 to 20% by weight.

Further, examples of the polypropylene-based block copolymer including a polypropylene homopolymer component or a copolymer component mainly including propylene, and a copolymer component of propylene and ethylene and/or α-olefin include a propylene-ethylene block copolymer, a (propylene)-(propylene-ethylene) block copolymer, a (propylene)-(propylene-ethylene-1-butene) block copolymer, a (propylene)-(propylene-ethylene-1-hexene) block copolymer, a (propylene)-(propylene-1-butene) block copolymer, a (propylene)-(propylene-1-hexene) block copolymer, a (propylene-ethylene)-(propylene-ethylene-1-butene) block copolymer, a (propylene-ethylene)-(propylene-ethylene-1-hexene) block copolymer, a (propylene-ethylene)-(propylene-1-butene) block copolymer, a (propylene-ethylene)-(propylene-1-hexene) block copolymer, a (propylene-1butene)-(propylene-ethylene) block copolymer, a (propylene-1butene)-(propylene-ethylene-1-butene) block copolymer, a (propylene-1butene)-(propylene-ethylene-1-hexene) block copolymer, a (propylene-1-butene)-(propylene-1-butene) block copolymer, a (propylene-1butene)-(propylene-1-hexene) block copolymer and the like.

In the case of using a polypropylene-based resin as the thermoplastic polymer in the present invention, a crystalline propylene homopolymer and a polypropylene-based block copolymer including a polypropylene homopolymer component or a copolymer component mainly including propylene, and a copolymer component of propylene and ethylene and/or α-olefin having 4 to 12 carbon atoms are preferable. A polypropylene-based block copolymer including a polypropylene homopolymer component or a copolymer component mainly including propylene, and a copolymer component of propylene and ethylene and/or α-olefin having 4 to 12 carbon atoms are more preferable.

<Thermoplastic Polymer Molded Product>

The present invention also provides a thermoplastic polymer molded product in which the stabilizer composition (the stabilizer composition according to the first aspect or the stabilizer composition according to the second aspect) of the present invention described above is compounded in an amount of 0.005 to 5 parts by weight (preferably 0.005 to 1 part by weight and particularly preferably 0.01 to 1 part by weight) with respect to 100 parts by weight of the thermoplastic polymer. The compounding amount of the stabilizer composition of the present invention is the same as that of the thermoplastic polymer composition of the present invention described above since there is an effect of preventing deterioration of the thermoplastic polymer during a molding process by compounding the stabilizer composition of the present invention in an mount of 0.005 part by weight or more with respect to 100 parts by weight of the thermoplastic polymer, and there is an advantage that it is difficult for a bleeding phenomenon to occur in which the stabilizer appears on the surface of the polymer by compounding the stabilizer composition of the present invention in an mount of 5 part by weight or less with respect to 100 parts by weight of the thermoplastic polymer. Further, the same examples of the thermoplastic polymers for the thermoplastic polymer composition of the present invention described above can be included as the thermoplastic polymer used in the thermoplastic polymer molded product of the present invention.

The thermoplastic polymer molded product of the present invention is obtained by compounding the stabilizer composition of the present invention into the thermoplastic polymer as described above and molding the mixture into a desired form. The molding method is not particularly limited, and includes a conventionally known method such as press molding, injection molding, extrusion molding, blow molding, heat molding, and compression molding. Also in such a thermoplastic polymer molded product of the present invention, the resistance to discoloration at high temperature of the thermoplastic polymer is improved compared with the conventional one by compounding the stabilizer composition of the present invention described above.

<Method of Stabilizing Thermoplastic Polymer>

The present invention also provides a method of stabilizing the thermoplastic polymer in which the stabilizer composition (the stabilizer composition according to the first aspect or the stabilizer composition according to the second aspect) of the present invention described above is compounded into the thermoplastic polymer. According to the method of stabilizing the thermoplastic polymer of the present invention, the resistance to discoloration at high temperature of the thermoplastic polymer is improved compared with the conventional one, and the stabilization can be attempted.

Also in the method of stabilizing the thermoplastic polymer of the present invention, for the same reasons described above for the thermoplastic polymer molded product, the stabilizer composition of the present invention is preferably compounded at 0.005 to 5 parts by weight with respect to 100 parts by weight of the thermoplastic polymer, more preferably compounded at 0.005 to 1 part by weight, and particularly preferably compounded at 0.01 to 1 part by weight. The same examples of the thermoplastic polymers for the thermoplastic polymer composition of the present invention described above can be included as the thermoplastic polymer used in the method of stabilizing the thermoplastic polymer of the present invention.

<Method of Manufacturing Thermoplastic Polymer Composition>

Furthermore, the present invention also provides a method of manufacturing the thermoplastic polymer composition, in which the stabilizer composition (the stabilizer composition according to the first aspect or the stabilizer composition according to the second aspect) of the present invention described above is compounded in an amount of 0.005 to 5 parts by weight (preferably 0.005 to 1 part by weight and particularly preferably 0.01 to 1 part by weight) with respect to 100 parts by weight of the thermoplastic polymer. According to such a method, the thermoplastic polymer composition of the present invention described above that can improve the resistance to discoloration at high temperature of the thermoplastic polymer compared with the conventional one can be preferably manufactured. The same examples of the thermoplastic polymers for the thermoplastic polymer composition of the present invention described above can be included as the thermoplastic polymer used in such method of manufacturing the thermoplastic polymer composition.

EXAMPLES

Referring to Examples and Comparative Examples below, the present invention is explained in more detail. However, the present invention is not limited to these.

Example 1

A 500-ml four-neck flask was charged with 94.1 g of a dialkylphenol composition (2,4-di-tert-amylphenol manufactured by Liaoning Jinhuan Corporation) having 2,4-di-tert-pentylphenol as a main component and containing the compound represented by the formula (1), 0.7 g of p-toluene sulfonic acid monohydrate, and 3.8 g of 78% sulfuric acid solution during stirring. Moreover, the compound represented by the formula (1) contained in the dialkylphenol composition was subjected to liquid chromatography analysis in the same manner as described above, and the area percentage was 7.7%. To this mixture, a solution in which 9.7 g of acetaldehyde was diluted with 23 g of xylene was added dropwise over two hours while the temperature was maintained at 20 to 50° C. After completion of the dropwise addition, the temperature inside a chamber was increased to 90° C., and kept at the same temperature for 3 hours. After the constant temperature period was completed, 126 g of xylene, 47 g of water, and 94 g of 25% sodium hydroxide solution were added, and a water phase was separated by separation at about 80° C. After 47 g of water was added to an oil phase and washed, the water phase was separated by separation. The water content was removed from the obtained oil phase by azeotropic dehydration in a condition of a temperature inside the chamber of up to 94° C. and an inner pressure of up to 22.6 kPa. The oil phase after the dehydration was 234 g.

15.5 g of acrylic acid and 44.6 g of triethylamine were added to the oil phase after the dehydration at room temperature, and 21.7 g of phosphorus oxychloride was added dropwise for 5 hours at a temperature inside the chamber of about 40° C. After completion of the dropwise addition, the mixture was kept at the same temperature for 3 hours, 49 g of water was added, and the temperature was increased to 76° C. After stirring for 1 hour at the same temperature, a water phase was separated by separation. An oil phase was washed with 49 g of water, and this process was repeated twice. The oil phase after washing with water was condensed in a condition of a temperature inside the chamber of up to 95° C. and an inner pressure of up to 17.8 kPa, and cooled to 60° C. 61 g of methanol and 0.17 g of 10% sodium carbonate solution were added to this oil phase, and cooled to 11° C., to precipitate a crystal. The crystal was filtered, washed with methanol, and dried at about 80° C. under reduced pressure, to obtain 55 g of a white crystal. The obtained white crystal was subjected to liquid chromatography analysis in the same manner as described above, and the content of the bisphenol monoester compound represented by the formula (4) was 1.2% in area percentage.

Further, in order to isolate the bisphenol monoester-based compound represented by the formula (4) from the obtained white crystal, preparative isolation was performed through the following method: That is, an isolated product was obtained by, using Large Scale Preparative System (8A type manufactured by Shimadzu Corporation) with Sumipax ODS A-210 (20 mm in diameter×25 cm in height, diameter of filler: 5 μm) as a column and a mixed solution of water and methanol as a mobile phase, keeping the ratio of methanol in the mobile phase at 94.5% for 60 minutes, and performing the preparative isolation in a condition of keeping the ratio of methanol at 100% for 15 minutes. Further, the isolated product was subjected to preparative isolation again by, using Large Scale Preparative System (8A type manufactured by Shimadzu Corporation) with Sumipax ODS A-210 (20 mm in diameter×25 cm in height, diameter of filler: 5 μm) as a column and a mixed solution of water and methanol as a mobile phase, keeping the ratio of methanol in the mobile phase at 93% for 60 minutes, and performing the preparative isolation in the condition of keeping the ratio of methanol at 100% for 15 minutes.

Figure 2:
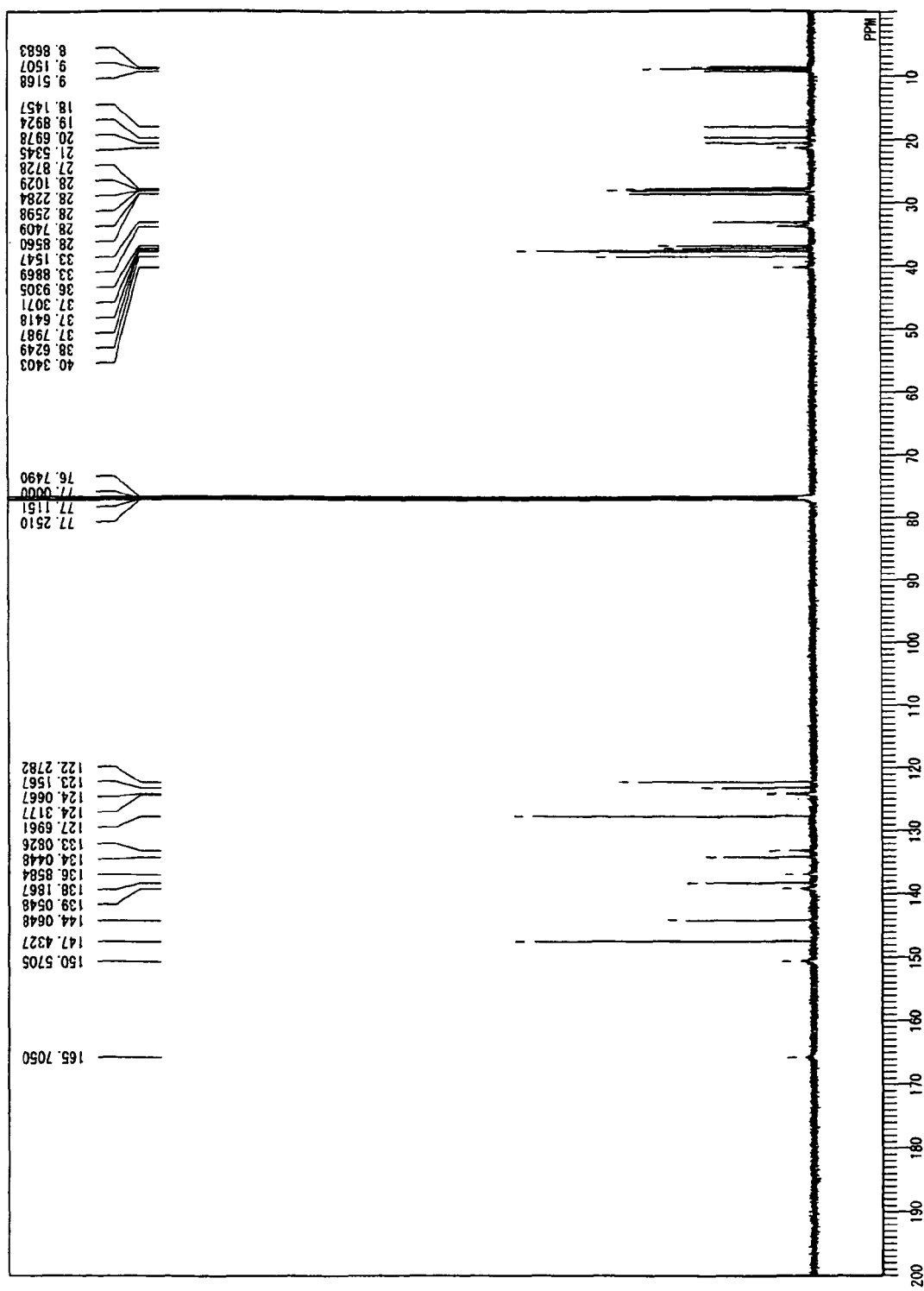
FIG. 2 is a $^{13}$C NMR spectrum of the bisphenol monoester-based compound represented by the formula (4) and fractionated in Example 1.

The obtained bisphenol monoester-based compound represented by the formula (4) was subjected to NMR spectrum measurement with tetramethylsilane as an inner standard using ECA-500 (manufactured by JEOL Ltd.). A $^1$H NMR (500.16 MHz, CDC 13) spectrum is shown in FIG. 1, and a $^{13}$C NMR spectrum (125.77 MHz, CDC 13) is shown in FIG. 2.

Comparative Example 1

A 500-ml four-neck flask was charged with 117.5 g of a dialkylphenol composition (2,4-di-tert-amylphenol manufactured by Goi Chemical Co., Ltd.) having 2,4-di-tert-pentylphenol as a main component and containing the compound represented by the formula (1), 0.9 g of p-toluene sulfonic acid monohydrate, and 4.7 g of 78% sulfuric acid solution during stirring. Moreover, the compound represented by the formula (1) contained in the dialkylphenol composition was subjected to liquid chromatography analysis in the same manner as described above, and the area percentage of the formula (1) was 0.2%. To this mixture, a solution in which 12.1 g of acetaldehyde was diluted with 28 g of xylene was added dropwise over two hours while the temperature was maintained at 20 to 60° C. After completion of the dropwise addition, the temperature inside a chamber was increased to 90° C., and kept at the same temperature for 3 hours. After the constant temperature period was completed, 157 g of xylene, 59 g of water, and 11.7 g of 25% sodium hydroxide solution were added, and a water phase was separated by separation at about 80° C. After 59 g of water was added into an oil phase and washed, the water phase was separated by separation. The water content was removed from the obtained oil phase by azeotropic dehydration in a condition of a temperature inside the chamber of up to 98° C. and an inner pressure of up to 22.9 kPa. The oil phase after the dehydration was 316 g.

20.6 g of acrylic acid and 59.4 of triethylamine were added to the oil phase after the dehydration at room temperature, and 29 g of phosphorus oxychloride was added dropwise for 5 hours at a temperature inside the chamber of about 40° C. After completion of the dropwise addition, the mixture was kept at the same temperature for 1 hours, 65 g of water was added, and the temperature was increased to 80° C. After stirring for 1 hour at the same temperature, a water phase was separated by separation. An oil phase was washed with 65 g of water, and this process was repeated twice. The oil phase after washing with water was condensed in a condition of a temperature inside the chamber of up to 87° C. and an inner pressure of up to 12.2 kPa, and cooled to 60° C. 81 g of methanol and 0.22 g of 10% sodium carbonate solution were added to this oil phase, and cooled to 11° C., to precipitate a crystal. The crystal was filtered, washed with methanol, and dried at about 80° C. under reduced pressure, to obtain 97 g of a white crystal. The obtained white crystal was subjected to liquid chromatography analysis in the same manner as described above, and the content of the compound represented by the formula (4) was less than 0.05% in area percentage.

Example 2

40 g of the bisphenol monoester-based stabilizer composition obtained in Example 1 and 10 g of the bisphenol monoester-based stabilizer composition obtained in Comparative Example 1 were mixed with a mortar, to prepare a mixture of a stabilizer composition in a powder form. The mixture prepared was subjected to liquid chromatography analysis in the same manner as in Example 1, and the content of the compound represented by the formula (4) was 0.9% in area percentage.

Example 3

10 g of the bisphenol monoester-based stabilizer composition obtained in Example 1 and 40 g of the bisphenol monoester-based stabilizer composition obtained in Comparative Example 1 were mixed with a mortar, to prepare a mixture of a stabilizer composition in a powder form. The mixture prepared was subjected to liquid chromatography analysis in the same manner as in Example 1, and the content of the compound represented by the formula (4) was 0.2% in area percentage.

Example 4

5 g of the bisphenol monoester-based stabilizer composition obtained in Example 1 and 45 g of the bisphenol monoester-based stabilizer composition obtained in Comparative Example 1 were mixed with a mortar, to prepare a mixture of a stabilizer composition in a powder form. The mixture prepared was subjected to liquid chromatography analysis in the same manner as in Example 1, and the content of the compound represented by the formula (4) was 0.1% in area percentage.

Example 5

0.05 Part by weight of calcium stearate and 0.5 part by weight of the stabilizer composition obtained in Example 1 were dry-blended into 100 parts by weight of a propylene-ethylene block copolymer (MI: 9 to 10 g/10 minutes) (230° C., 2.16 kg) (manufactured by Sumitomo Chemical Co., Ltd.) as the thermoplastic polymer, the mixture was placed into a Labo Plastomill mixer (manufactured by Toyo Seiki Seisaku-Sho, Ltd.), and was kneaded at 250° C. at a rotational frequency of 30 rotations/minute for 5 minutes, to obtain a thermoplastic polymer composition compounded with the stabilizer obtained in Example 1. The obtained thermoplastic polymer composition was taken out from the mixer, pressed at 230° C. with heat press, and a sheet shaped thermoplastic polymer molded product having a size of 120 mm×120 mm×1 mm was obtained.

Example 6

A thermoplastic polymer molded product was obtained in the same manner as in Example 5, except that the mixture of the stabilizer composition obtained in Example 2 was used.

Example 7

A thermoplastic polymer molded product was obtained in the same manner as in Example 5, except that the mixture of the stabilizer composition obtained in Example 3 was used.

Example 8

A thermoplastic polymer molded product was obtained in the same manner as in Example 5, except that the mixture of the stabilizer composition obtained in Example 4 was used.

Example 9

A thermoplastic polymer molded product was obtained in the same manner as in Example 5, except that the stabilizer composition obtained in Example 1 was compounded in an amount of 0.1 part by weight with respect to 100 parts by weight of the thermoplastic polymer.

Comparative Example 2

A thermoplastic polymer molded product was obtained in the same manner as in Example 5, except that the stabilizer composition obtained in Comparative Example 1 was used.

<Evaluation Test: Resistance to Discoloration at High Temperature>

Yellowness index (YI) values of the thermoplastic polymer molded products obtained in Examples 5 to 9 and Comparative Example 2 were measured using a colorimeter (CM-3500d manufactured by Konica Minolta Holdings, Inc.) in accordance with JIS K7105, and the resistance to discoloration at high temperature was evaluated. The smaller the measured YI value is, the better the resistance to discoloration at high temperature is meant to be. The result is shown in Table 1.

TABLE 1

| | COMPOUNDING AMOUNT OF THERMOPLASTIC POLYMER (PARTS BY WEIGHT) | COMPOUNDING AMOUNT OF CALCIUM STEARATE (PARTS BY WEIGHT) | STABILIZER COMPOSITION | | | RESISTANCE TO DISCOLORATION AT HIGH TEMPERATURE (YI) |
| --- | --- | --- | --- | --- | --- | --- |
| | | | TYPE | COMPOUNDING AMOUNT (PARTS BY WEIGHT) | CONTENT OF COMPOUND REPRESENTED BY FORMULA (4) (%) | |
| EXAMPLE 5 | 100 | 0.05 | EXAMPLE 1 | 0.5 | 1.2 | 15.65 |
| EXAMPLE 6 | 100 | 0.05 | EXAMPLE 2 | 0.5 | 0.9 | 14.33 |
| EXAMPLE 7 | 100 | 0.05 | EXAMPLE 3 | 0.5 | 0.2 | 17.14 |
| EXAMPLE 8 | 100 | 0.05 | EXAMPLE 4 | 0.5 | 0.1 | 17.99 |
| EXAMPLE 9 | 100 | 0.05 | EXAMPLE 1 | 0.1 | 1.2 | 10.64 |
| COMPARATIVE EXAMPLE 2 | 100 | 0.05 | COMPARATIVE EXAMPLE 1 | 0.5 | <0.05 | 18.47 |

Moreover, in Table 1, the content of the compound represented by the formula (4) means the content of the compound represented by the formula (4) shown in area percentage (%) in the liquid chromatography analysis. From Table 1, it is found that the resistance to discoloration at high temperature of any of the thermoplastic polymer molded products in Examples 5 to 9 is improved compared with that of the thermoplastic polymer molded product in Comparative Example 2.

Although the present invention has been described and illustrated in detail, it is clearly understood that the same is by way of illustration and example only and is not to be taken by way of limitation, the scope of the present invention being interpreted by the terms of the appended claims.

What is claimed is:

1. A bisphenol monoester-based stabilizer composition comprising a bisphenol monoester-based compound represented by the following formula (3):

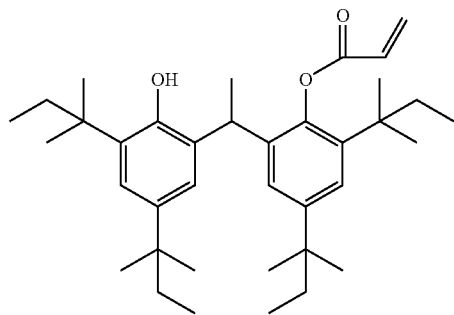

(3)

mainly and a compound represented by the following formula (4):

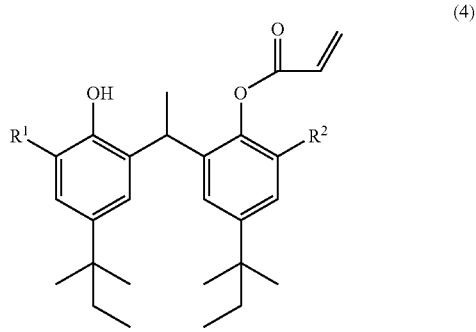

(4)

wherein any one of $R^1$ and $R^2$ represents a tert-pentyl group and the other represents a 1,2-dimethylpropyl group, wherein the compound represented by following formula (4) is contained in an area percentage by liquid chromatography analysis of 0.1 to 1.2%.

2. A thermoplastic polymer composition comprising a thermoplastic polymer and the bisphenol monoester-based stabilizer composition according to claim 1.

3. The thermoplastic polymer composition according to claim 2, comprising 0.005 to 5 parts by weight of the bisphenol monoester-based stabilizer composition with respect to 100 parts by weight of the thermoplastic polymer.

4. A thermoplastic polymer molded product comprising a thermoplastic polymer and 0.005 to 5 parts by weight of the bisphenol monoester-based stabilizer composition according to claim 1 with respect to 100 parts by weight of the thermoplastic polymer.

5. A method of stabilizing a thermoplastic polymer comprising compounding the bisphenol monoester-based stabilizer composition according to claim 1 into the thermoplastic polymer.

6. A method of manufacturing a thermoplastic polymer composition comprising compounding 0.005 to 5 parts by weight of the bisphenol monoester-based stabilizer composition according to claim 1 into 100 parts by weight of the thermoplastic polymer.

* * * * *